United States Patent
Ismail et al.

(10) Patent No.: US 6,750,763 B2
(45) Date of Patent: Jun. 15, 2004

(54) SYSTEM AND METHOD FOR MEASURING OIL CONDITION IN LARGE ENGINES

(75) Inventors: Keith N. Ismail, El Paso, TX (US); Oscar Alfonso Lecea, El Paso, TX (US); Steven Douglas Thomson, El Paso, TX (US)

(73) Assignee: Delphi Technologies, Inc., Troy, MI (US)

( * ) Notice: Subject to any disclaimer, the term of this patent is extended or adjusted under 35 U.S.C. 154(b) by 94 days.

(21) Appl. No.: 10/066,832

(22) Filed: Feb. 4, 2002

(65) Prior Publication Data

US 2003/0145647 A1 Aug. 7, 2003

(51) Int. Cl.[7] .................................................. B60Q 1/00
(52) U.S. Cl. .................... 340/450.3; 340/439; 340/450; 340/450.2; 73/54.01; 73/54.02; 123/73 AD; 123/196 R; 324/698
(58) Field of Search .......................... 340/450.3, 450.2, 340/457, 450, 603, 609, 438, 439, 449; 123/196 R, 196 S, 73 AD, 179.19; 60/605.3; 702/50; 324/698; 73/54.01, 54.02

(56) References Cited

U.S. PATENT DOCUMENTS

| | | | | |
|---|---|---|---|---|
| 5,159,910 A | * | 11/1992 | Ninoiya et al. | 123/196 AB |
| 5,789,665 A | * | 8/1998 | Voelker et al. | 73/53.05 |
| 5,896,841 A | * | 4/1999 | Nemoto et al. | 123/381 |
| 6,377,879 B2 | * | 4/2002 | Kanno | 701/29 |
| 6,557,396 B2 | | 5/2003 | Ismail et al. | |
| 6,575,018 B2 | * | 6/2003 | Berndorfer et al. | 73/54.01 |
| 6,590,402 B2 | * | 7/2003 | Wang et al. | 324/698 |

* cited by examiner

*Primary Examiner*—Davetta W. Goins
(74) *Attorney, Agent, or Firm*—Jimmy L. Funke

(57) ABSTRACT

A system for measuring oil condition in large engines includes a bypass valve that is installed in a lubrication system along a fluid line between an oil pan and an engine. The bypass valve communicates with a measurement chamber and when energized by a control module, the bypass valve diverts oil from the lubrication system to the measurement chamber. An oil condition sensor is disposed within the measurement chamber and is used to determine the condition of the oil that is diverted to the chamber. After the condition of the oil is determined, the bypass valve is energized to release the oil from the measurement chamber back into the lubrication system.

20 Claims, 1 Drawing Sheet

SYSTEM AND METHOD FOR MEASURING OIL CONDITION IN LARGE ENGINES

1. Technical Field

The present invention relates generally to oil condition sensors.

2. Background of the Invention

Automatically monitoring the quality of oil in an engine alerts owners in a timely fashion when maintenance should be performed as dictated by the actual condition of the oil. Performing maintenance when it is actually required is preferred over following a predetermined, one-size-fits-all schedule that might be too long or too short for any given vehicle, depending on the way the vehicle is driven. If too long a period elapses between maintenance, an engine can be damaged. On the other hand, conducting maintenance when it is not needed is wasteful both in terms of labor and in terms of natural resources. For example, if an engine doesn't require an oil change but nevertheless receives one, oil is in effect wasted.

Accordingly, oil condition sensors have been provided for small engines, e.g., motor vehicle engines, that measure various parameters of lubricating oil, and to generate warning signals when maintenance is due as indicated by the condition of the oil. Among the parameters that are typically measured are oil temperature, contamination, and degradation. Unfortunately, many larger industrial engines, e.g., large diesel generators and heavy equipment engines, do not include any means for sensing the condition of the lubricating oil. Thus, in order to maximize the life of larger industrial engines, the lubricating oil must be constantly sampled and tested, e.g., in a laboratory.

The present invention understands that in order to incorporate a device that can continuously monitor the quality of the lubricating fluid in a large engine it may be necessary to make major modifications, such as modifying an existing oil pan or installing a new oil pan. As such, retrofitting an existing engine to include an oil condition sensor can be very cost prohibitive.

The present invention has recognized these prior art drawbacks, and has provided the below-disclosed solutions to one or more of the prior art deficiencies.

SUMMARY OF THE INVENTION

A system for determining oil condition includes an engine, an oil pan, and a pump in communication therewith. A bypass valve is installed between the engine and the oil pan. Accordingly, the bypass valve is energizable to divert oil to a measurement chamber where the condition of the oil is determined.

In a presently preferred embodiment, an oil condition sensor is disposed in the measurement chamber. Moreover, the system includes a control module that is electrically connected to the bypass valve and the oil condition sensor. The control module sends a signal to the bypass valve to cause the bypass valve to divert oil to the measurement chamber. Also, the control module receives a signal from the oil condition sensor that represents the condition of the oil. Preferably, the system includes a warning device that receives a signal from the control module when the condition of the oil falls outside a predetermined operating range.

In another aspect of the present invention, a method for determining oil condition includes installing at least one bypass valve in a lubrication system and installing a measurement chamber in fluid communication with the bypass valve. Then, the bypass valve is energized to divert oil to a measurement chamber where the condition of the oil that has been diverted is determined.

In yet another aspect of the present invention, a lubrication system includes an engine and an oil pan. A bypass valve is installed in a fluid line between the engine and the oil pan and a measurement chamber communicates with the bypass valve. In this aspect of the present invention, a control module is electrically connected to the bypass valve. The control module includes logic means for energizing the bypass valve in order to divert oil from the lubrication system to the measurement chamber where the condition of the oil is determined.

The present invention will now be described, by way of example, with reference to the accompanying drawings, in which:

DESCRIPTION OF AN EMBODIMENT OF THE INVENTION

Figure 1:
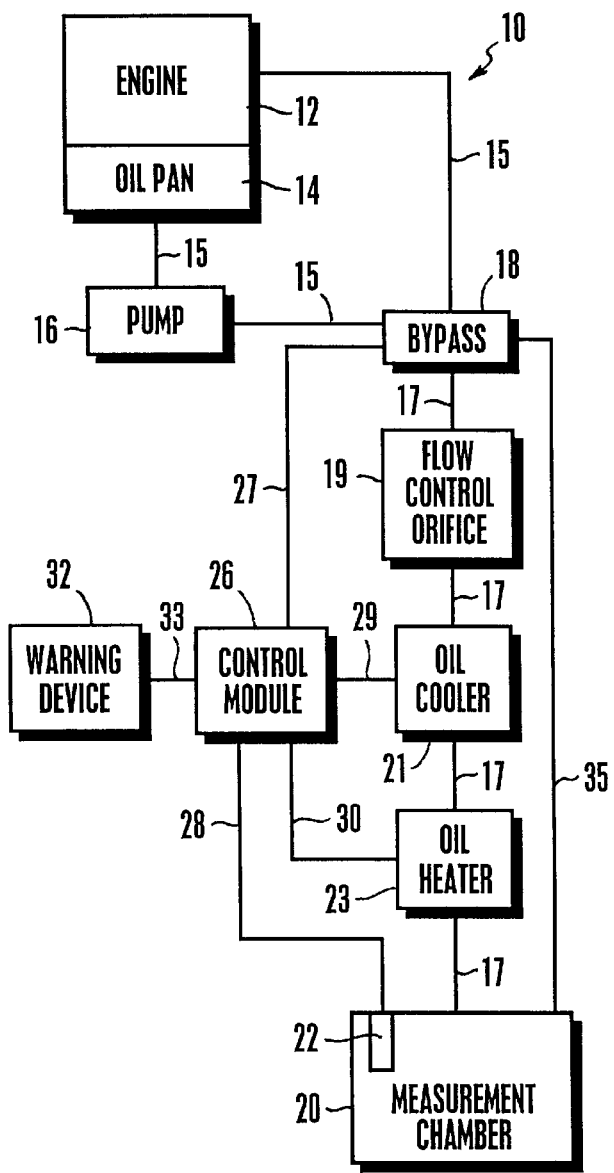
FIG. 1 is a block diagram representing an engine lubrication system.

Referring initially to FIG. 1, a vehicle lubrication system is shown and generally designated 10. FIG. 1 shows that the lubrication system includes an engine 12 and an oil reservoir, e.g., an oil pan 14, in fluid communication with the engine 12 via fluid line 15. As shown in FIG. 1, an oil pump 16 is installed along fluid line 15 so that it is in fluid communication with the engine 12 and the oil pan 14. The oil pump 16 pumps oil from the oil pan 14 to the engine 12 in order to lubricate moving parts within the engine 12, e.g., the rocker arms, and cam shafts.

FIG. 1 shows a bypass valve 18 installed between the pump 16 and the engine 12. When energized, the bypass valve 18 allows oil in the lubrication system 10 to pass into a measurement chamber 20 in which an oil condition sensor 22 is installed. It is to be appreciated that the oil condition sensor 22 is, e.g., a standard oil condition sensor that is found on many light vehicles. Thus, oil can be bypassed from the lubrication system 10 to the measurement chamber 20 via a bypass fluid line 17 so that the condition of the oil can be determined. It is also to be appreciated that the bypass valve 18 can also be installed between the oil pan 14 and the pump 16.

As shown in FIG. 1, a flow control orifice 19 is installed downstream of the bypass 18 along the bypass fluid line 17. It is to be understood, that the flow control orifice 19 restricts the flow of oil through the bypass fluid line 17. Moreover, it is to be appreciated that the flow control orifice 19 can be downstream of the bypass 18, i.e., outside the bypass 18, or it can be within the bypass 18, e.g., within the outlet of the bypass 18 leading to the bypass fluid line 17.

FIG. 1 shows an oil cooler 21 and an oil heater 23 that are installed along the bypass fluid line 17. It is to be understood that the oil cooler 21 and the oil heater 23 can be used to decrease and increase the temperature of the oil bypassed to the measurement chamber, respectively. Thus, at the beginning of the testing, the oil will be at the required start temperature before being allowed to pass through a temperature gradient, as described below. It is to be understood that the oil cooler 21 and the oil heater 23 include a thermostat for regulating the temperature of the oil passing therethrough.

As shown in FIG. 1, a control module 26 is connected to the bypass valve 18 via an electrical line 27. As shown, the control module 26 is connected to the oil condition sensor 22 via electrical line 28. Moreover, the control module 26 is connected to the oil cooler 21 and the oil heater 23 by electrical line 29 and electrical line 30, respectively. Accordingly, when it is time to check the condition of the oil, the control module 26 sends a signal to the bypass valve 18 in order to energize the bypass valve 18 and divert oil to the measurement chamber 20. If necessary, the control module 26 sends a signal to the oil cooler 21 or the oil heater 23 in order to cool or heat the oil before it enters the measurement chamber 20. The control module 26 also receives a signal from the oil condition sensor 22 representing the condition of the oil.

FIG. 1 shows a warning device 32 that is connected to the control module 26 via electrical line 33. Thus, when the condition of the oil within the lubrication system 10 falls below a predetermined critical level, the warning device 32 can be activated to signal the owner or operator of the engine 12 that the oil needs to be changed before the engine 12 is damaged. It is to be appreciated that the warning device 32 can be an audible warning device, e.g., a buzzer or audible alarm. On the other hand, the warning device 32 can also be a visual warning device, e.g., a warning lamp or other visual display. After the condition of the oil is determined, it can be released back into the system 10 through a return fluid line 35 installed from the measurement chamber 20 to the bypass 18.

While the preferred implementation of the control module 26 is a chip such as a digital signal processor, it is to be understood that the logic disclosed below can be executed by other digital processors, such as by a personal computer. Or, the control module 26 may be any computer, including a Unix computer, or OS/2 server, or Windows NT server, or a laptop computer, or a hand held computer.

The control module 26 includes a series of computer-executable instructions, as described below, which will allow the control module 26 to divert the oil in the lubrication system 10 to a measurement chamber 20 where the condition of the oil can be determined using a standard oil condition sensor 22. These instructions may reside, for example, in RAM of the control module 26.

Alternatively, the instructions may be contained on a data storage device with a computer readable medium, such as a computer diskette. Or, the instructions may be stored on a DASD array, magnetic tape, conventional hard disk drive, electronic read-only memory, optical storage device, or other appropriate data storage device. In an illustrative embodiment of the invention, the computer-executable instructions may be lines of compiled C++ compatible code.

The flow charts herein illustrate the structure of the logic of the present invention as embodied in computer program software. Those skilled in the art will appreciate that the flow charts illustrate the structures of computer program code elements including logic circuits on an integrated circuit, that function according to this invention. Manifestly, the invention is practiced in its essential embodiment by a machine component that renders the program elements in a form that instructs a digital processing apparatus (that is, a computer) to perform a sequence of function steps corresponding to those shown.

Figure 2:
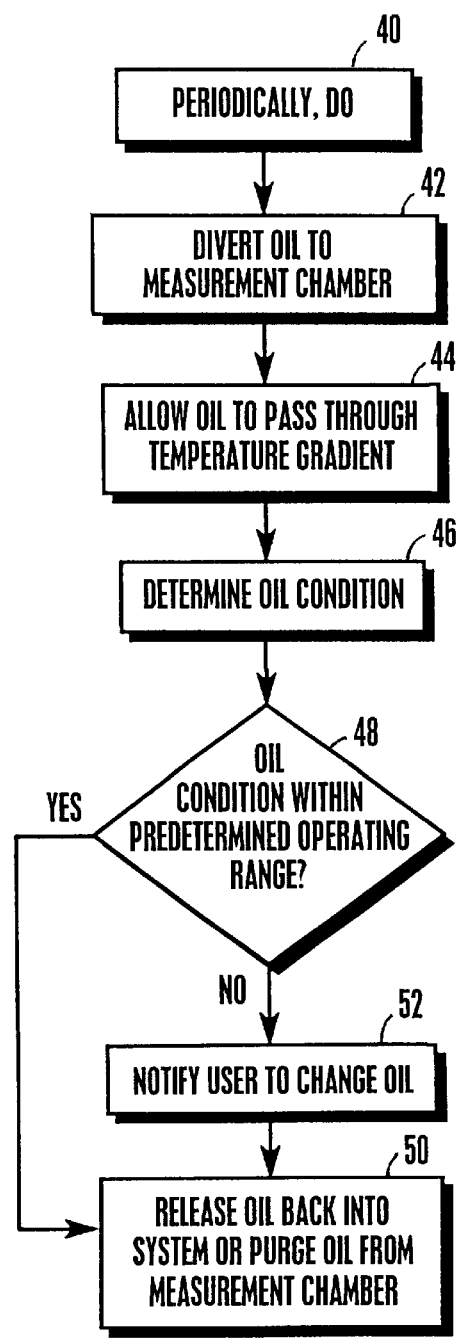
FIG. 2 is a flow chart representing the overall logic of the present invention.

Referring to FIG. 2, the overall logic of the present invention is shown. Commencing at block 40, a do loop is entered wherein the succeeding steps are periodically performed to determine the condition of the oil in the lubrication system 10. Moving to block 42, the bypass valve 18 is energized so that oil from the lubrication system 10 is diverted to the measurement chamber 20. Thereafter, at block 44, the oil in the measurement chamber 20 is allowed to pass through a temperature gradient, e.g., the oil is allowed to cool. Continuing to block 46, while the oil passes through the temperature gradient, the condition of the oil is determined.

Proceeding to decision diamond 48, it is determined whether the condition of the oil is within a predetermined operating range. If so, the logic continues to block 50 where the oil in the measurement chamber 20 is released back into the lubrication system. However, if the condition of the oil is not within the predetermined operating range, the logic moves to block 52 where the control module 26 sends a signal to the warning device 32 in order to notify the owner or operator of the engine to change the oil in the engine. Thereafter, the logic continues to block 50 where the oil is released back into the lubrication system 10 or purged from the measurement chamber 20.

With the configuration of structure and logic described above, it is to be appreciated that the system and method for determining oil condition in large engines can be used to determine the condition of oil in large industrial engines, e.g., diesel generators, without having to take a sample of the oil and send it to a laboratory. Moreover, the condition of the oil within the lubrication system 10 can be constantly monitored using a standard oil condition sensor without having to retrofit an existing oil pan.

While the particular SYSTEM AND METHOD FOR DETERMINING OIL CONDITION IN LARGE ENGINES as herein shown and described in detail is fully capable of attaining the above-described objects of the invention, it is to be understood that it is the presently preferred embodiment of the present invention and thus, is representative of the subject matter which is broadly contemplated by the present invention, that the scope of the present invention fully encompasses other embodiments which may become obvious to those skilled in the art, and that the scope of the present invention is accordingly to be limited by nothing other than the appended claims, in which reference to an element in the singular is not intended to mean "one and only one" unless explicitly so stated, but rather "one or more." All structural and functional equivalents to the elements of the above-described preferred embodiment that are known or later come to be known to those of ordinary skill in the art are expressly incorporated herein by reference and are intended to be encompassed by the present claims. Moreover, it is not necessary for a device or method to address each and every problem sought to be solved by the present invention, for it is to be encompassed by the present claims. Furthermore, no element, component, or method step in the present disclosure is intended to be dedicated to the public regardless of whether the element, component, or method step is explicitly recited in the claims. No claim element herein is to be construed under the provisions of 35 U.S.C. section 112, sixth paragraph, unless the element is expressly recited using the phrase "means for."

What is claimed is:

1. A system for determining oil condition, comprising:
    at least one engine;
    at least one oil pan;
    at least one oil pump in communication with the engine and the oil pan;
    at least one oil measurement chamber, an oil condition sensor being disposed in the chamber; and at least one bypass valve installed between the engine and the oil pan, the bypass valve being energizable to divert oil to the measurement chamber where the condition of the oil is determined.

2. The system of claim 1, further comprising:

a control module electrically connected to the bypass valve and the oil condition sensor, the control module sending a signal to the bypass valve to cause the bypass valve to divert oil to the measurement chamber, the control module receiving a signal from the oil condition sensor representing the condition of the oil.

3. The system of claim 2, further comprising:

a warning device receiving a signal from the control module when the condition of the oil falls outside a predetermined operating range.

4. The system of claim 1, further comprising:

at least one oil cooler installed between the bypass valve and the measurement chamber.

5. The system of claim 1, furthercomprising:

at least one oil heater installed between the bypass valve and the measurement chamber.

6. A method for determining oil condition, comprising the acts of:

installing at least one bypass valve in a lubrication system;

installing a measurement chamber in fluid communication with the bypass valve;

installing an oil condition sensor in the measurement chamber;

energizing the bypass valve to divert oil to a measurement chamber; and using the oil condition sensor, determining the condition of the oil within the measurement chamber.

7. The method of claim 6, further comprising the act of: cooling the oil.

8. The method of claim 6, further comprising the act of: heating the oil.

9. The method of claim 6, further comprising the act of: releasing an oil test additive to the measurement chamber.

10. The method of claim 6, further comprising the act of: allowing the oil to pass through a temperature gradient.

11. The method of claim 6, further comprising the acts of: comparing the condition of the oil to a predetermined operating range; and based thereon, activating a warning device when the condition of the oil falls outside the predetermined operating range.

12. The method of claim 6, further comprising the act of: releasing the oil back into the lubrication system.

13. The method of claim 6, further comprising the act of: purging the oil from the measurement chamber.

14. A lubrication system, comprising:

at least one engine;

at least one oil pan;

at least one bypass valve installed in a fluid line between the engine and the oil pan;

at least one measurement chamber in fluid communication with the bypass valve; and a control module electrically connected to the bypass valve, the control module including logic means for energizing the bypass valve to divert oil from the lubrication system to the measurement chamber where the condition of the oil is determined by at least one oil condition sensor.

15. The system of claim 14, further comprising:

at least one oil condition sensor disposed within the measurement chamber, the oil condition sensor being electrically connected to the control module.

16. The system of claim 14, wherein the control module further includes logic means for receiving a signal representing the oil condition from the oil condition sensor.

17. The system of claim 16, wherein the system further includes a warning device electrically connected to the control module and the control module further includes logic means for activating the warning device when the oil condition falls outside a predetermined operating range.

18. The system of claim 14, wherein the control module further includes logic means for energizing the bypass valve in order to release the oil back into the lubrication system after the oil condition has been determined.

19. The system of claim 14, further comprising:

at least one oil cooler, the control module further including logic means for energizing the oil cooler to cool the oil.

20. The system of claim 14, further comprising:

at least one oil heater, the control module further including logic means for energizing the oil heater to heat the oil.

* * * * *